(12) United States Patent
Sudin et al.

(10) Patent No.: US 10,828,142 B2
(45) Date of Patent: Nov. 10, 2020

(54) INTRALUMINAL DEVICE

(71) Applicant: RAPID MEDICAL LTD., Yokneam (IL)

(72) Inventors: Yuri Sudin, Modiin (IL); Aharon Friedman, Haifa (IL); Ronen Eckhouse, Shimshit (IL)

(*) Notice: Subject to any disclaimer, the term of this patent is extended or adjusted under 35 U.S.C. 154(b) by 243 days.

(21) Appl. No.: 15/773,375

(22) PCT Filed: Nov. 4, 2016

(86) PCT No.: PCT/IB2016/001740
§ 371 (c)(1),
(2) Date: May 3, 2018

(87) PCT Pub. No.: WO2017/077393
PCT Pub. Date: May 11, 2017

(65) Prior Publication Data
US 2018/0318062 A1    Nov. 8, 2018

Related U.S. Application Data

(60) Provisional application No. 62/250,767, filed on Nov. 4, 2015.

(51) Int. Cl.
*A61F 2/01*    (2006.01)

(52) U.S. Cl.
CPC .......... *A61F 2/01* (2013.01); *A61F 2002/016* (2013.01); *A61F 2250/0015* (2013.01); *A61F 2250/0023* (2013.01)

(58) Field of Classification Search
CPC ...... A61F 2/01; A61F 2/02; A61F 2/04; A61F 2/82; A61F 2/86; A61F 2/90;
(Continued)

(56) References Cited

U.S. PATENT DOCUMENTS

2003/0040771 A1* 2/2003 Hyodoh .................. A61F 2/90
606/200
2003/0153971 A1    8/2003 Chandrasekaran
(Continued)

FOREIGN PATENT DOCUMENTS

WO    WO 96/41589 A1    12/1996
WO    WO 01/10351 A1    2/2001
(Continued)

OTHER PUBLICATIONS

Supplementary Partial European Search Report dated Sep. 27, 2019, in corresponding European Application No. 16861684.
(Continued)

*Primary Examiner* — Ashley L Fishback
(74) *Attorney, Agent, or Firm* — Finnegan, Henderson, Farabow, Garrett & Dunner, L.L.P.

(57) ABSTRACT

In one exemplary embodiment, an intraluminal device may include elongated structure formed of a plurality of wires. The intraluminal device may also include a plurality of sets of looped wires longitudinally located at an intermediate area of the elongated structure and the plurality of sets may be spaced circumferentially about the structure and being configured to cooperate with each other to form a plurality of clot entry openings. At least one grouping of woven wires may be longitudinally located adjacent the intermediate area and the at one grouping of woven wires may be configured such that when an opening force is exerted on the elongated structure, the at least one grouping provides structural support to hold open first interstices between the plurality of sets of looped wires.

17 Claims, 10 Drawing Sheets

(58) Field of Classification Search
CPC .......... A61F 2002/016; A61F 2002/823; A61F 2002/825; A61F 2250/0023
See application file for complete search history.

(56) References Cited

U.S. PATENT DOCUMENTS

2004/0153117 A1    8/2004   Clubb et al.
2012/0053596 A1    3/2012   Gordon
2014/0330305 A1*  11/2014   Rood ........................ A61F 2/01
                                                        606/200

FOREIGN PATENT DOCUMENTS

WO    WO 2010/111666 A1    9/2010
WO    WO 2013/102848 A2    7/2013
WO    WO 2014/061013 A1    4/2014

OTHER PUBLICATIONS

International Search Report for International Application No. PCT/IB16/01740, dated Apr. 6, 2017 (1 page total).
Written Opinion of the International Searching Authority for International Application No. PCT/IB16/01740 dated Apr. 6, 2017 (9 pages total).

* cited by examiner

INTRALUMINAL DEVICE

PRIORITY

This application is a U.S. national stage entry under 35 U.S.C. § 371 of International Application No. PCT/IB2016/001740, filed Nov. 4, 2016, which claims the benefit of priority from U.S. Provisional Application No. 62/250,767, filed Nov. 4, 2015, each of the above-referenced disclosures of which is herein incorporated by reference in its entirety.

FIELD

This disclosure relates to intravascular and/or intraluminal medical devices that are configured to retrieve an obstruction from human blood vessels. Obstructions to be retrieved can include clots and clot material.

SUMMARY

The disclosed embodiments may include an intraluminal device including an elongated structure formed of a plurality of wires. The intraluminal device may include a plurality of sets of looped wires longitudinally located at an intermediate area of the elongated structure. The plurality of sets may be spaced circumferentially about the structure and configured to cooperate with each other to form a plurality of clot entry openings. At least one grouping of woven wires may be longitudinally located adjacent the intermediate area and may be configured such that when an opening force is exerted on the elongated structure, the at least one grouping may provide structural support to hold open first interstices between the plurality of sets of looped wires. In response to the opening force, second interstices may be formed between wires in the at least one grouping of woven wires and the first interstices in the looped wire sets may be larger than the second interstices between wires in each of the at least one grouping.

In another embodiment, at least one grouping of the intraluminal device may include at least two groupings of woven wires, and each grouping may be spaced longitudinally from each other on opposite sides of the intermediate area containing the plurality of sets of looped wires. The at least two groupings of woven wires may cooperate with each other such that when an opening force is exerted on the wire structure, the at least two groupings provide structural support to hold open first interstices between the plurality of sets of looped wires. In response to the opening force, the second interstices may be formed between wires in each of the at least two groupings, and the first interstices in the looped wire sets may be larger than the second interstices between wires in each of the at least two groupings.

In another embodiment, the elongated structure of the intraluminal device may be formed of at least 8 wires, and each of the plurality of sets of looped wires may be formed of the same at least 8 wires as the at least one grouping of woven wires.

In another embodiment, the elongated structure of the intraluminal device may be formed of 12 wires that, in the intermediate area, may define six sets of looped wires. In the adjacent area, the 12 wires may collectively form the at least one grouping of woven wires. In another embodiment, each of the 12 wires may have a diameter of about 80 microns. In one embodiment, for example, each wire of the intraluminal device may have a diameter of about 75 microns. By way of another example, each wire of the intraluminal device may have a diameter between 60 and 85 microns.

In another embodiment, an intraluminal device may include an elongated structure formed of a plurality of wires. The intraluminal device may include a first region wherein the plurality of wires may be twisted to form a shaft and a second region, adjacent to the first region, wherein the plurality of wires may be woven to form a scaffold. The intraluminal device may also include a third region, adjacent to the second region, wherein the plurality of wires may be separated into sets of looped pairs to form a clot capture structure. The intraluminal device may also include a fourth region wherein the plurality of wires may be braided to form a dense filter configured to catch a blood clot.

In another embodiment, the elongated structure of the intraluminal device may be configured to transition between a collapsed position for delivery to a treatment site, and an expanded position in response to an opening force exerted thereon.

In another embodiment, the elongated structure of the intraluminal device may be configured such that, for example, when the opening force is applied, first interstices may be formed between wires in the second region, and second interstices may be formed between wires in the third region, such that the second interstices are larger than the first interstices.

In another embodiment, the elongated structure of the intraluminal device may be configured such that, for example, when the opening force is applied, third interstices are formed between wires in the fourth region, such that, for example, the third interstices are smaller than both the first interstices and the second interstices.

In another embodiment, the intraluminal device may include a fifth region, adjacent to the fourth region, and wherein the plurality of wires in the fifth region may be twisted to form an additional shaft. In another embodiment, the intraluminal device may include 12 wires and each wire may have a diameter of about 80 microns. In one embodiment, for example, each wire of the intraluminal device may have a diameter of about 75 microns. By way of another example, each wire of the intraluminal device may have a diameter between 60 and 85 microns.

In another embodiment, the elongated structure of the intraluminal device may be configured such that the opening force may be applied through axial movement of the first region. In yet another embodiment, the intraluminal device may include an additional second region of scaffold between the third region and the fourth region.

In another embodiment, an intraluminal device may include an elongated structure formed of a plurality of wires and the device may also include a plurality of cables each formed of a subset of the plurality of wires. The pairs of cables may cross each other at a plurality of intersection locations and at the plurality of intersection locations, wires from each pair of crossing cables may be unwound and woven together with wires from a paired crossing cable. Further, the wires of the crossing cables may be woven together at the intersection locations in a manner permitting the woven-together wires to move relative to each other when an opening force is applied to the elongated structure. Also, in response to the opening force exerted thereon, at the intersection locations, pairs of crossing cables may be configured to pivot relative to each other as the elongated structure transitions between a collapsed position for delivery to a treatment site, and an expanded clot capture position.

BRIEF DESCRIPTION OF THE DRAWINGS

The accompanying drawings, which are incorporated in and constitute a part of this specification, illustrate disclosed embodiments and, together with the description, serve to explain the disclosed embodiments.

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings. Wherever possible, the same reference numbers will be used throughout the drawings to refer to the same or like parts.

Figure 1:
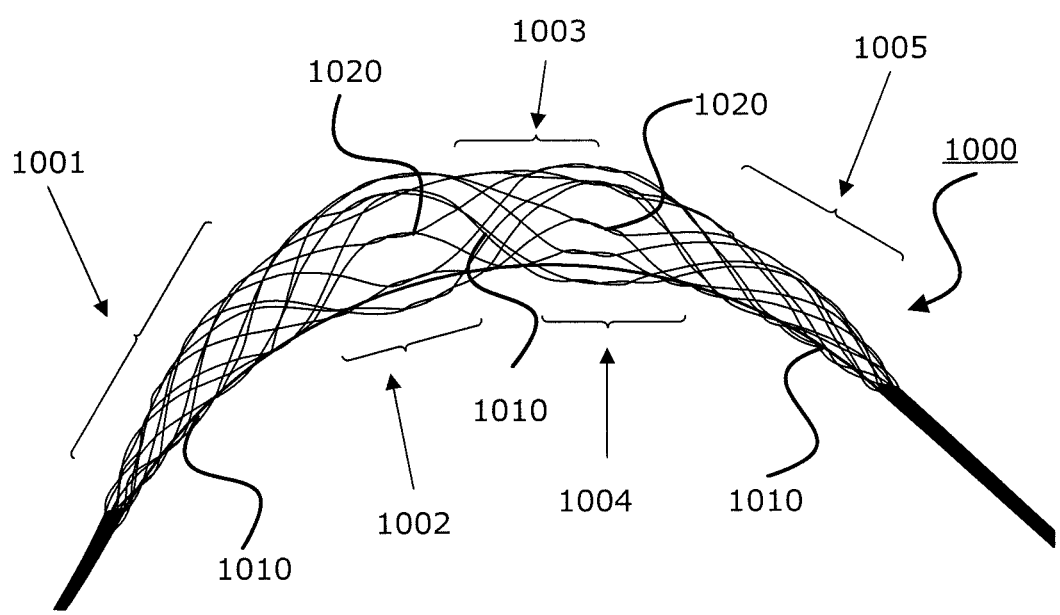
FIG. 1 is an illustration of an exemplary intraluminal device, consistent with at least one of the disclosed embodiments.
Figure 10:
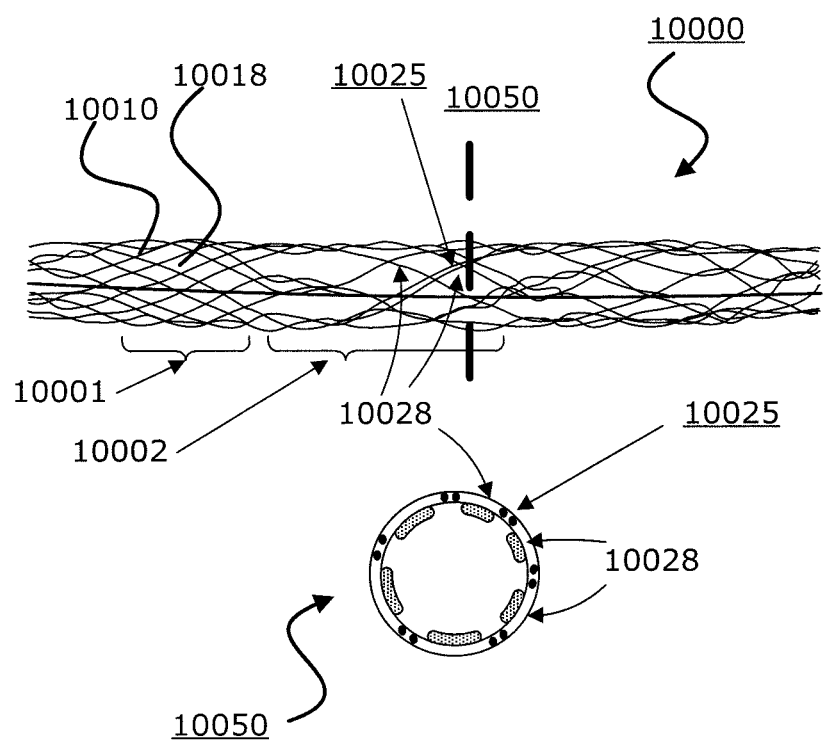
FIG. 10 is a further explanation of the regions of an intraluminal device consistent with at least one of the disclosed embodiments.

FIG. 1 illustrates an exemplary intraluminal device 1000 including five alternating wire zones 1001, 1002, 1003, 1004, and 1005. Zones 1001, 1003 and 1005 include groups of woven wires 1010 and may provide structural support for zones 1002 and 1004. Additionally, since the openings between wires 1010 of zone 1 and 5 may be much smaller they also may provide a distal and proximal filter. (An example of variable sized openings is illustrated in FIG. 10, discussed below.) As a result, clot particles that might appear during the retrieval may be captured at these zones, for example. As further shown in FIG. 1, zones 1002 and 1004 may be constructed of looped wires 1020 to allow a large clot capturing area. And also shown in FIG. 1, zones 1001, 1003, and 1005 may be constructed by woven wires 1010. The number of zones illustrated are exemplary. More or less zones may be provided.

Figure 2:
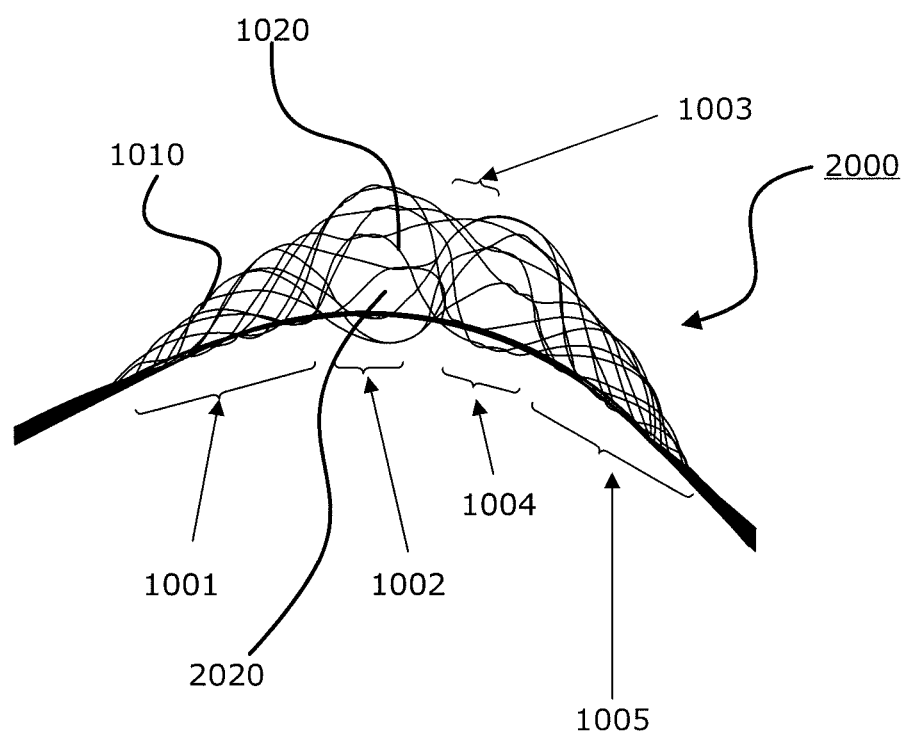
FIG. 2 is an illustration of another exemplary intraluminal device in accordance with at least one of the disclosed embodiments.

FIG. 2 illustrates an intraluminal device 2000 in a more open position than illustrated in FIG. 1, highlighting the clot entry cells 2020 that may be made from the looped wires 1020. As further shown in FIG. 2, zones 1002 and 1004 may be constructed of looped wires 1020 to allow a large clot capturing area.

Figure 3:
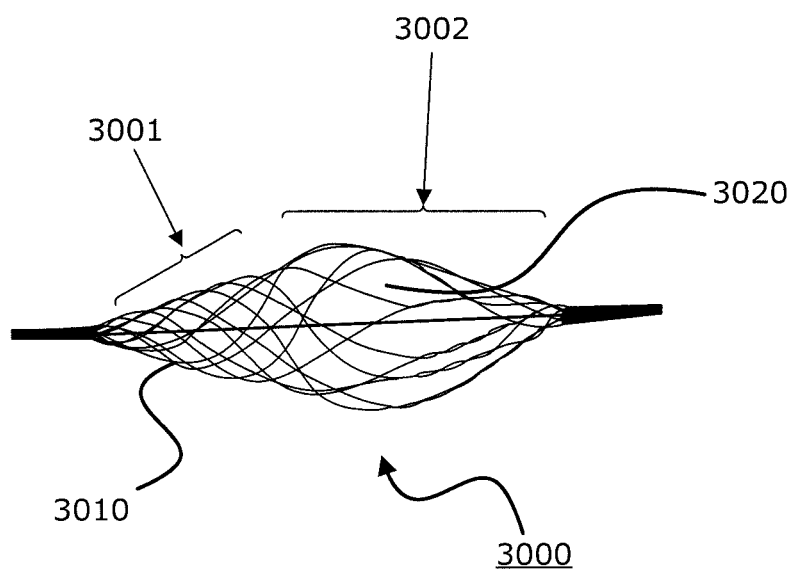
FIG. 3 is an illustration of another exemplary intraluminal device in accordance with at least one of the disclosed embodiments.

FIG. 3 illustrates yet another exemplary intraluminal device 3000. In this example, as shown in FIG. 3, the device 3000 may be configured so as to include only two different zones. Zone 3001 may be constructed from a group of woven wires 3010, such as for example, densely braided, which provides structural support for the device 3000. In addition, zone 3001 may also serve as a distal filter that prevents emboli from the distal vasculature. As also shown in FIG. 3, zone 3002 may be constructed from wires which are looped which are longitudinally located and provide the clot entry zone 3020. Additionally, zone 3001 may, for example, give structural support and may also serve as a distal filter. As further shown in FIG. 3, zone 3002 may be the clot entering zone.

Figure 4:
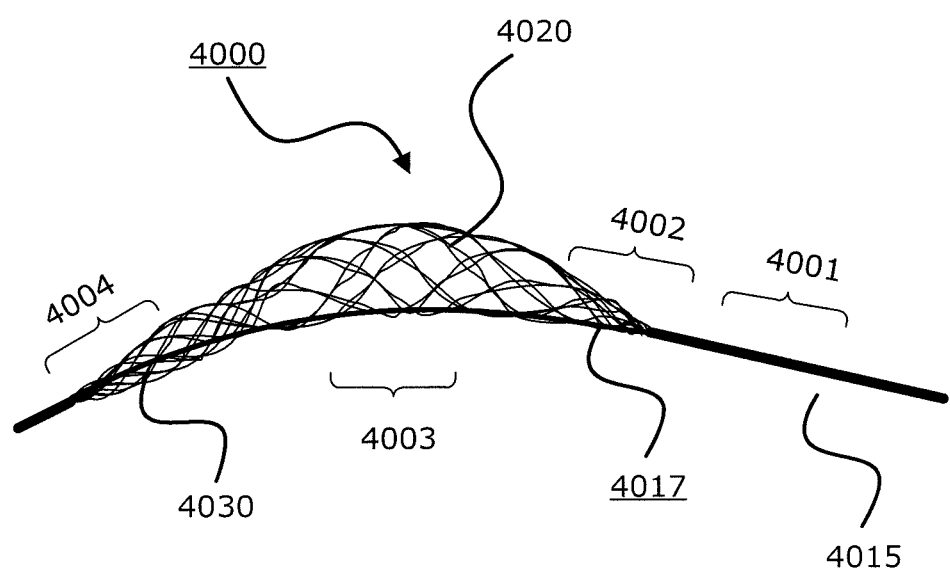
FIG. 4 is an illustration of another exemplary intraluminal device in accordance with at least one of the disclosed embodiments.

FIG. 4 illustrates yet another exemplary intraluminal device 4000 with four regions. In the first region 4001, the wires may be twisted or coiled to form a shaft 4015. In the second region 4002, the wires may be woven to from a scaffold 4017 that supports the opening of the third region 4003. In the third region 4003, the wires may be woven set in looped pairs to form a clot capture structure 4020. For example, the wires of the third region n 4003 may be loosely looped or loosely coupled. Further, the fourth region 4004 may be woven to form a distal filter 4030 that captures distal emboli or clot particles. The fourth region 4004 may also serve as a scaffold for the third region 4003.

Figure 5:
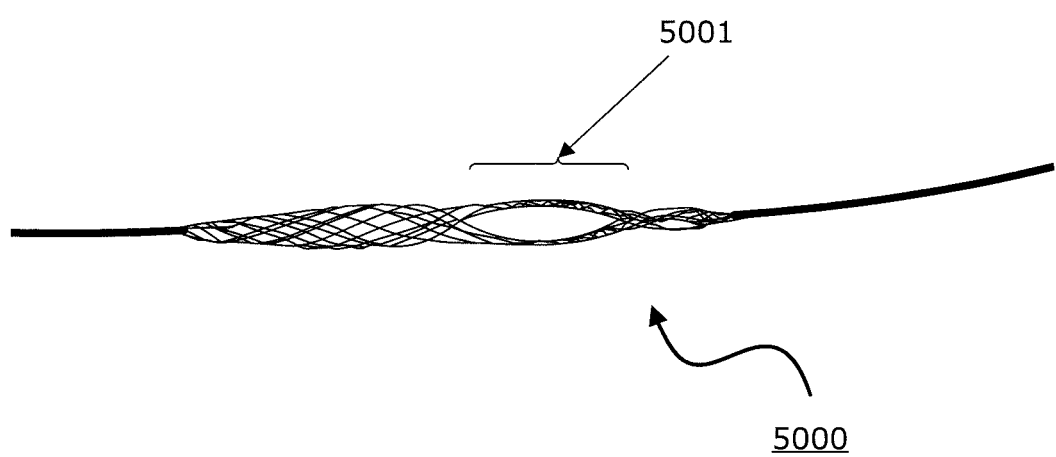
FIG. 5 is an illustration of another exemplary intraluminal device in accordance with at least one of the disclosed embodiments.

FIG. 5 illustrates yet another exemplary intraluminal device 5000. For example, as shown in FIG. 5, the clot opening region 5001 may be woven from three wires that are looped together. Further, the number of wires that are looped together may be greater than two.

Figure 6:
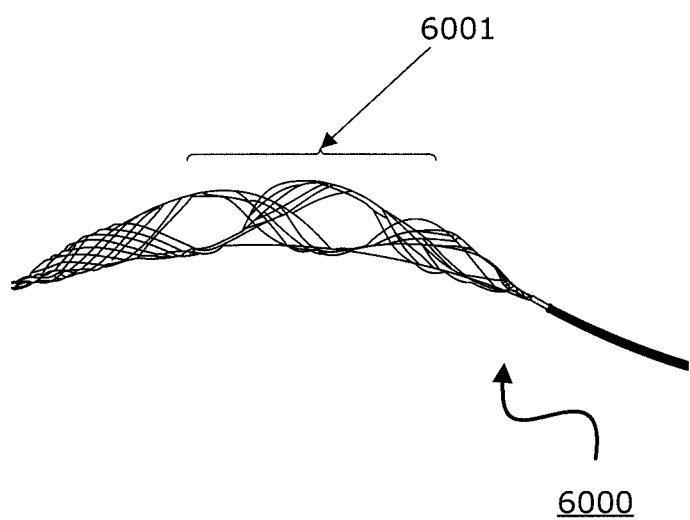
FIG. 6 is an illustration of another exemplary intraluminal device in accordance with at least one of the disclosed embodiments.

FIG. 6 is illustrates yet another exemplary intraluminal device 6000. For example, as shown in FIG. 6, the clot opening region 6001 may be woven from three wires that are loosely looped together. Further, the number of wires that are looped together may be greater than two.

Figure 7:
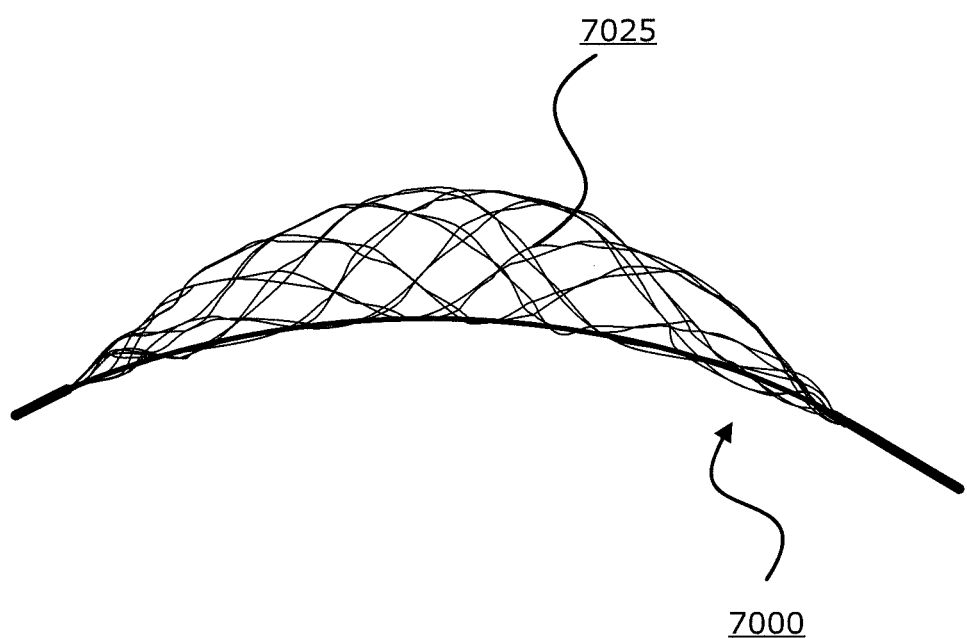
FIG. 7 is an illustration of another exemplary intraluminal device in accordance with at least one of the disclosed embodiments.

FIG. 7 illustrates yet another exemplary intraluminal device 7000. For example, as shown in FIG. 7, the device 7000 may include six cables 7025, in which each cable 7025 may include paired wires. This may create a strong but flexible crossing. And this may further allow, for example, the device 7000 to achieve a flexible structure with a high radial force.

Figure 8:
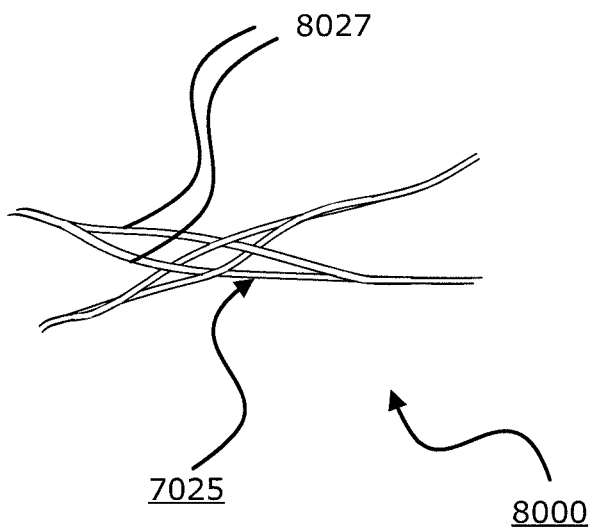
FIG. 8 is an illustration of exemplary cable interweaving, such as is disclosed in connection with FIG. 7.

FIG. 8 illustrates an example of cable interweaving 8000, as discussed above. Each cable 7025, for example, may be made from a looped pair of wires 8027 that are woven with a pair of wires from a crossing cable. As a result, for example, a semi-flexible and strong crossing point may be achieved.

Figures 9A, 9B:
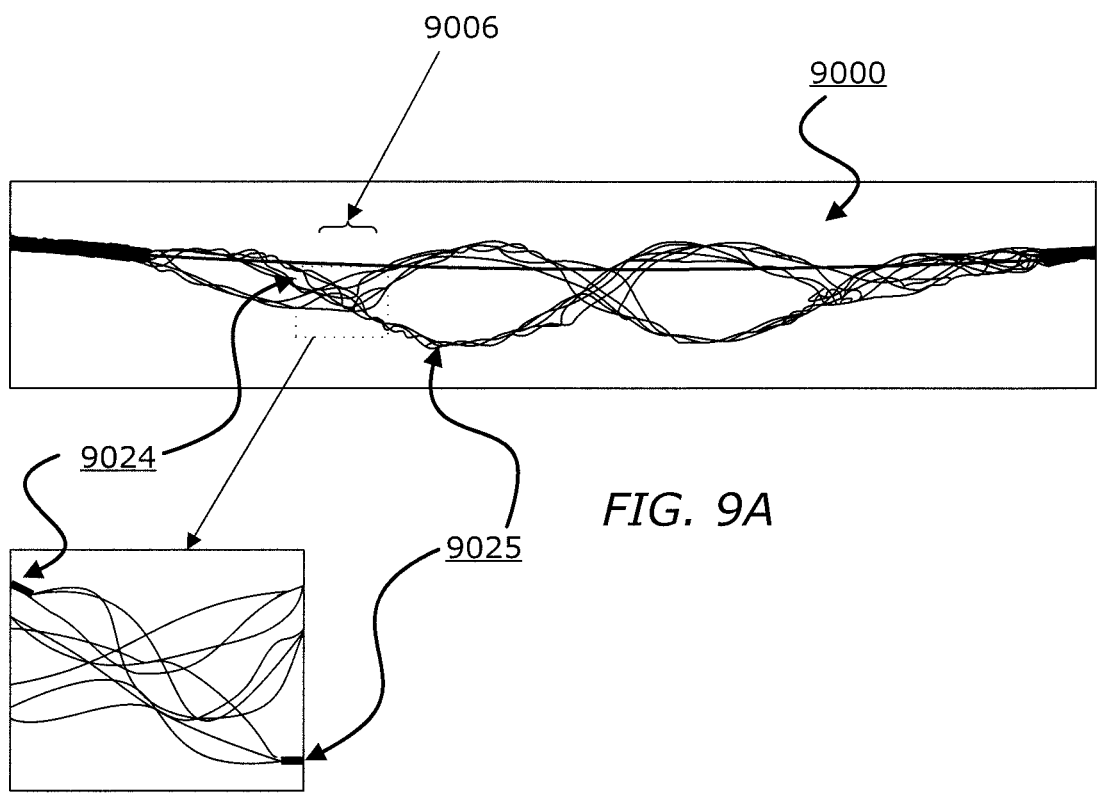
FIG. 9A is an illustration of another exemplary intraluminal device in accordance with at least one of the disclosed embodiments.
FIG. 9B is an enlarged view of a portion of the exemplary intraluminal device shown in FIG. 9A.

FIGS. 9A-9B illustrate yet another exemplary intraluminal device. As shown in FIG. 9A, the cables, for example, may be made from three wires that are unwound and then woven together with the wires from the crossing cable. FIG. 9B also illustrates the cable crossing point 9006 where the cables (including cables 9024 and 9025) are unwound and woven back together.

As discussed above in connection with FIG. 1, FIG. 10 illustrates device 10000 with variable-sized openings. Region 10001 includes groups of woven wires 10010 adjacent to intermediate location 10002, and may provide structural support for intermediate location 10002. Specifically, the groupings of woven wires 10010 in region 10001 can provide the support to hold open the first interstices 10028. The first interstices 10028 are larger than the second interstices 10018, where the second interstices are present in region 10001. Cross section 10050 depicts how the cables 10025 are circumferentially displaced in the intermediate location 10002. (The lines making up the ring depicted in cross section 10050 are to indicate the generally circumferential displacement of the cables 10025 about a central region. Moreover, the dotted regions depicted in the cross section 10050 internal to the first interstices 10028 are used to depict the relatively large openings provided for clot entry in the intermediate location 10002.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. An intraluminal device including an elongated structure formed of a plurality of wires, the intraluminal device comprising:
    a plurality of sets of looped wires longitudinally located at an intermediate area of the elongated structure, the plurality of sets being spaced circumferentially about the structure and being configured to cooperate with each other to form a plurality of clot entry openings and wherein the sets of looped wires cross each other at a plurality of intersection locations; and
    at least one grouping of woven wires, longitudinally located adjacent the intermediate area, wherein the at one grouping of woven wires is configured such that when an opening force is exerted on the elongated structure, the at least one grouping provides structural support to hold open first interstices between the plurality of sets of looped wires, and wherein in response to the opening force, second interstices are formed between wires in the at least one grouping of woven wires, the first interstices in the looped wire sets being larger than the second interstices between wires in each of the at least one grouping.

2. The intraluminal device of claim 1, wherein the at least one grouping includes at least two groupings of woven wires, each grouping being spaced longitudinally from each other on opposite sides of the intermediate area containing the plurality of sets of looped wires, wherein the at least two groupings of woven wires cooperate with each other such that when an opening force is exerted on the wire structure, the at least two groupings provide structural support to hold open first interstices between the plurality of sets of looped wires, and wherein in response to the opening force, second interstices are formed between wires in each of the at least two groupings, the first interstices in the looped wire sets being larger than the second interstices between wires in each of the at least two groupings.

3. The intraluminal device of claim 1, wherein the elongated structure is formed of at least 12 wires, and wherein each of the plurality of sets of looped wires is formed of the same at least 12 wires as the at least one grouping of woven wires.

4. The intraluminal device of claim 1, wherein the structure is formed of 12 wires that, in the intermediate area, define six sets of looped wires, and wherein in the adjacent area, the 12 wires collectively form the at least one grouping of woven wires.

5. The intraluminal device of claim 4, wherein each of the 12 wires has a diameter of about 80 microns.

6. The intraluminal device of claim 5, wherein each of the 12 wires has a diameter of 75 microns.

7. An intraluminal device including an elongated structure formed of a plurality of wires, the intraluminal device comprising:
    a first region wherein the plurality of wires are twisted to form a shaft;
    a second region, adjacent to the first region, wherein the plurality of wires are woven to form a scaffold;
    a third region, adjacent to the second region, wherein the plurality of wires are separated into sets of looped pairs to form a clot capture structure, the sets of looped pairs being configured to cross each other at a plurality of intersection locations; and
    a fourth region wherein the plurality of wires are braided to form a dense filter configured to catch a blood clot.

8. The intraluminal device of claim 7, wherein the elongated structure is configured to transition between a collapsed position for delivery to a treatment site, and an expanded position in response to an opening force exerted thereon.

9. The intraluminal device of claim 8, wherein the elongated structure is configured such that when the opening force is applied, first interstices are formed between wires in the second region, and second interstices are formed between wires in the third region, such that the second interstices are larger than the first interstices.

10. The intraluminal device of claim 9, wherein the elongated structure is configured such that when the opening force is applied, third interstices are formed between wires in the fourth region, such that the third interstices are smaller than both the first interstices and the second interstices.

11. The intraluminal device of claim 8, wherein the elongated structure is configured such that the opening force is applied through axial movement of the first region.

12. The intraluminal device of claim 7, further comprising a fifth region, adjacent to the fourth region, and wherein the plurality of wires in the fifth region are twisted to form an additional shaft.

13. The intraluminal device of claim 7, wherein the plurality of wires includes 12 wires.

14. The intraluminal device of claim 13, wherein each of the 12 wires has a diameter of about 80 microns.

15. The intraluminal device of claim 14, wherein each of the 12 wires has a diameter of 75 microns.

16. The intraluminal device of claim 7, further comprising an additional second region of scaffold between the third region and the fourth region.

17. An intraluminal device including an elongated structure formed of a plurality of wires, the device comprising:
    a plurality of cables each formed of a subset of the plurality of wires, wherein pairs of cables cross each other at a plurality of intersection locations;
    wherein at the plurality of intersection locations, wires from each pair of crossing cables are unwound and woven together with wires from a paired crossing cable;
    wherein the wires of the crossing cables are woven together at the intersection locations in a manner permitting the woven-together wires to move relative to each other when an opening force is applied to the elongated structure; and wherein in response to the opening force exerted thereon, at the intersection locations, pairs of crossing cables are configured to pivot relative to each other as the elongated structure transitions between a collapsed position for delivery to a treatment site, and an expanded clot capture position.

* * * * *